(12) United States Patent
Li (10) Patent No.: US 7,087,220 B2
(45) Date of Patent: Aug. 8, 2006

(54) HIGH PH ANTIPERSPIRANT COMPOSITIONS OF ENHANCED EFFICACY

(75) Inventor: Zijun Li, Westfield, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 293 days.

(21) Appl. No.: 10/857,493

(22) Filed: May 28, 2004

(65) Prior Publication Data

US 2005/0265939 A1    Dec. 1, 2005

(51) Int. Cl.
*A61Q 15/00* (2006.01)
*A61Q 19/00* (2006.01)
*A61K 8/00* (2006.01)
*A61K 8/02* (2006.01)

(52) U.S. Cl. ............... 424/65; 424/66; 424/68; 424/400; 424/401

(58) Field of Classification Search ............... 424/65, 424/66, 68, 400, 401
See application file for complete search history.

(56) References Cited

U.S. PATENT DOCUMENTS

| | | |
|---|---|---|
| 4,017,599 A | 4/1977 | Rubino |
| 5,908,616 A | 6/1999 | Parekh |
| 5,955,064 A | 9/1999 | Giovanniello |
| 6,042,816 A | 3/2000 | Shen |
| 6,245,325 B1 | 6/2001 | Shen |
| 6,375,937 B1 | 4/2002 | Chopra |
| 6,436,381 B1 | 8/2002 | Carrillo |

FOREIGN PATENT DOCUMENTS

WO    WO 97/48371    12/1997

*Primary Examiner*—Shelley A. Dodson
(74) *Attorney, Agent, or Firm*—Arthur J. Plantamura (57) ABSTRACT

Aluminum and aluminum-zirconium antiperspirant compositions of enhanced efficacy and a pH value of at least 3.5 are provided that are made by reaction with insoluble, strongly alkaline strontium or calcium salts. The aluminum and aluminum-zirconium strontium or calcium compositions show high pH values with characteristic HPLC Band III to Band II ratios of at least 0.5. The basic aluminum halohydrate (or nitrate) solutions typically have aluminum to anion ratio of less that 1.9. The solution compositions are stable with respect to both HPLC Band III to Band II ratio and viscosity at concentrations of about 20% to about 40% by weight of anhydrous solid. The solid state compositions form hard sticks with low irritation, at low metal to chloride ratios of about 0.9 to about 1.2.

32 Claims, 3 Drawing Sheets

HIGH PH ANTIPERSPIRANT COMPOSITIONS OF ENHANCED EFFICACY

The invention relates to antiperspirant compositions of enhanced efficacy comprising aluminum and aluminum-zirconium antiperspirant actives that are reacted with insoluble, strongly alkaline strontium or calcium salts forming high pH, stable solutions and to methods of making the antiperspirant salt compositions.

BACKGROUND OF THE INVENTION

Typical antiperspirant products use aluminum and aluminum-zirconium salts to prevent perspiration or reduce underarm sweat production. The degree of sweat reduction is directly related to the effectiveness of the antiperspirant salts. In general, aluminum and aluminum-zirconium antiperspirants of enhanced efficacy are those salts that reduce perspiration to a greater extent than do the analogous conventional salts. Aluminum or aluminum-zirconium antiperspirant salts of enhanced efficacy usually involve those actives that either have low metals to chloride ratios or higher HPLC Band III to Band II area ratio or both. Antiperspirant salts of enhanced efficacy at low metals to chloride ratios generally have lower pH values; products with lower pH tend to increase the irritancy potential of the actives. Also, antiperspirant salts of enhanced efficacy that have higher HPLC Band III (or peak 4) to Band II (or peak 3) ratio of at least 0.5 with at least 70% aluminum species present in Band III and Band II are not stable in solution form and their preparation is lengthy and not economical.

U.S. Pat. No. 6,375,937 B1 and U.S. Pat. No. 6,436,381 B1 disclose aluminum-zirconium antiperspirant salts at low metals to chloride ratios of 0.9 to 1.2 said to have increased efficacy in comparison with those salts having higher metals to chloride ratios. The process of making the salts however comprises a task that generally involves diluting, heating and cooling of the aluminum hydroxychloride solution, mixing with zirconium glycinate solution and spray drying the final solution. It should be noted also that aluminum-zirconium salts at low metals to chloride ratios are very acidic. Such salts, when formulated into antiperspirant products such as sticks, can cause skin irritation and degradation of the fragrance. Further, the sticks tend to become soft and develop an acidic odor over time, thus becoming aesthetically undesirable.

U.S. Pat. No. 6,726,901 B2 discloses an anhydrous antiperspirant composition containing aluminum-zirconium salt with low metals to chloride ratio. That reference mentions that it is possible to neutralize some of the acidity of the salt by adding a basic material to the aqueous solution during its manufacture. The antiperspirant efficacy of the salt, however, tends to decrease as the neutralization changes the properties of the antiperspirant salt. A stabilizing basic material is added separately in the formulation to prevent the degradation of the antiperspirant composition and to minimize acid odor so as not to diminish the efficacy of the salt. Four categories of stabilizing basic materials are mentioned: salts formed by a strong base and a weak acid; amino acids that are basic; salts formed by a strong base and an amino acid include calcium glycinate and strontium glycinate; and inorganic bases that are not soluble in water such as calcium oxide and strontium oxide. No distinction is made between the four classes, or within each of the four classes, in terms of effectiveness. Furthermore, in that disclosure the basic materials are introduced in the antiperspirant formulations. These materials are not introduced in the antiperspirant salts.

WO 97/48371 describes a topical formulation for reducing skin irritation that involves an aqueous soluble strontium cation. Strontium nitrate is selected as the anti-irritant salt component. While the formulation containing aqueous soluble strontium salt can be used in different products, no level of efficacy is apparent for that antiperspirant product.

U.S. Pat. No. 4,017,599 discloses an aluminum-zirconium antiperspirant composition buffered with an amino compound of alkaline and alkaline earth salts. In an Example, calcium glycinate is prepared by mixing glycine with calcium carbonate at elevated temperature, which is then reacted in-situ with aluminum hydroxybromide and zirconium hydroxybromide. When the same method is employed to generate calcium glycinate in-situ with aluminum hydroxychloride and zirconium hydroxychloride, solution gelling was observed upon heating.

U.S. Pat. No. 5,955,065 presents a topical antiperspirant composition comprising a dermatological acceptable anhydrous carrier vehicle having suspended an aluminum or an aluminum-zirconium antiperspirant salt and a water soluble calcium salt. This reference contains no disclosure of calcium salt being directly introduced to the antiperspirant active.

U.S. Pat. No. 6,042,816 describes a method of stabilizing an aqueous solution of enhanced efficacy aluminum-zirconium antiperspirant salt containing an effective amount of a water soluble calcium salt and an effective amount of a water soluble amino acid against rapid degradation of HPLC peak 4 (Band III) to peak 3 (Band II) ratio of the salt. The soluble salts are readily dissolved in water or in an aqueous solution of antiperspirant salt. As a soluble calcium salt, calcium chloride dihydrate is demonstrated in all the examples. It is clearly stated that only calcium provides the stabilization of enhanced efficacy antiperspirant salts. It does not teach the use of insoluble, strongly alkaline salts such as calcium oxide or strontium hydroxide. The aluminum salt used in the patent is ⅚ basic aluminum chlorohydrate (ACH) wherein the aluminum to chloride mole ratio is about 1.9:1 to 2.1:1.

U.S. Pat. No. 6,245,325 which a continuation-in-part of the continuation of the application resulting in above U.S. Pat. No. 6,042,816, broadens the compositional claims of U.S. Pat. No. 6,042,816 and as well as the composition application; however, the latter disclosure maintains the use of water soluble calcium compounds and does not move beyond the definition of a method of stabilizing an aqueous solution of enhanced efficacy aluminum-zirconium antiperspirant salt containing an effective amount of a soluble calcium salt and an effective amount of a water soluble amino acid against rapid degradation of HPLC peak 4 (Band III) to peak 3 (Band II) ratio of the salt.

U.S. Pat. No. 5,908,616 describes basic aluminum halides and nitrates having enhanced efficacy with aluminum to anion mole ratio of about 1.2 to about 1.8 and at a concentration of about 30%–40% by weight of anhydrous solid. The compositions have HPLC Band II of at least 50% and Band III of less than 20%. The composition, however, does not provide a higher HPLC Band III to Band II area ratio of at least 0.5.

Based on an overview of the known prior art it is apparent that it is highly desirable to provide aluminum and aluminum-zirconium salts of enhanced efficacy that are economical, to have the aluminum and aluminum-zirconium salts that have excellent skin aesthetics and that have the aluminum and aluminum-zirconium solutions which not only have enhanced efficacy, but are also stable.

SUMMARY OF THE INVENTION

According to the present invention, it has been discovered that aluminum and aluminum-zirconium antiperspirant compositions of enhanced efficacy can be obtained upon the reaction of an insoluble, strongly alkaline salt of either strontium or calcium with aluminum or aluminum-zirconium compounds. The invention also encompasses the method of making such compositions. These antiperspirant actives made with these insoluble, strongly alkaline strontium and/or calcium salts demonstrate higher pH values with characteristic HPLC Band III to Band II area ratios of at least 0.5. The compositions in solution form are stable with respect of both HPLC Band III to Band II ratio and the viscosity at concentrations of about 20% to about 40% by weight of anhydrous solid. The compositions formulated in solid state form such as an antiperspirant stick provide harder texture with no irritation, especially at lower metal to chloride ratios of about 0.9 to about 1.2.

The basic aluminum halohydrate (or nitrate) solutions used in the present invention typically have an aluminum to anion mole ratio of less than about 1.9, i.e., about 1.0 to about 1.8, preferably about 1.0 to about 1.7 and most preferably about 1.2 to about 1.6. The basic aluminum halohydrate (or nitrate) solution is made by the reaction of aluminum powder with aluminum halide (or nitrate) or the corresponding acid at an elevated temperature of greater than about 80° C. Insoluble, strongly alkaline strontium or calcium salts can be added to the basic aluminum halohydrate (or nitrate) solution and heated to the appropriate temperature to make the salt of enhanced efficacy by a process referred to as the indirect process. The insoluble, strongly alkaline strontium or calcium salts may also be added to an aluminum halide (or nitrate) or the corresponding acid solution and reacted with aluminum powder, by a procedure referred to as the direct process. An amino acid can be added during or near the end of reaction.

Additionally, the aluminum salt of enhanced efficacy, prepared by either the direct or indirect process, can be further modified by treatment with a zirconium compound (or glycinate) having a chloride to zirconium ratio of about 0.8 to about 2, at a temperature of from about room temperature to about reflux for a suitable period of time, to obtain an aluminum-zirconium antiperspirant salt of greater enhanced efficacy.

DETAILED DESCRIPTION OF THE INVENTION

In the process of the present invention it has been found that an increase in both pH and efficacy of aluminum or aluminum-zirconium antiperspirant salts can be obtained upon the reaction of an insoluble, strongly alkaline salt of either strontium or calcium or the mixture of both, with aluminum or aluminum-zirconium compounds, respectively.

The resulting aqueous compositions comprise about 20% to about 40% by weight of anhydrous solid, preferably about 25% to about 35% anhydrous solid, about 50% to about 70% of water, about 0.1% to about 2% by weight strontium or calcium, preferably about 0.3% to about 1% by weight of strontium and / or calcium, about 0% (in the case of non-zirconium antiperspirants) to about 8% by weight of amino acid, preferably about 3% to about 6% by weight of amino acid. Such aqueous solution of aluminum (in the absence of amino acid) or aluminum-zirconium are stable with respect of both HPLC Band III to Band II area ratio and the viscosity of the solution.

The insoluble, strongly alkaline calcium and strontium salts may be applied alone or as a blend of calcium and strontium salts. Generally, the higher the metals to chloride ratio, the lesser the amount of insoluble, strongly alkaline calcium or strontium salts or blended calcium/strontium salts are needed to increase the pH values of the compositions.

Preferred insoluble, strongly alkaline strontium salts include strontium hydroxide and strontium oxide and mixtures thereof. The amount of the insoluble, strongly alkaline strontium salt used in aqueous solution should be about 0.1% to about 2% by weight strontium, preferably about 0.3% to about 1.5% by weight strontium.

Preferred insoluble, strongly alkaline calcium salts include calcium oxide and calcium hydroxide and mixture thereof. The amount of the reacted calcium salt used in the final aqueous solution is about 0.1% to about 2% by weight calcium, preferably about 0.3% to about 1.5%, and most preferably about 0.5% to about 1% by weight calcium. The amount of calcium present in the solutions depends on the total concentration of the solution and the aluminum to chloride ratio.

Amino acids are known to stabilize Al—Zr antiperspirant salts and include glycine, alanine, lysine, ornithine, citrulline, proline, hydroxyproline, cysteine, threonine, valine, serine, methionine, glutamic acid, aspartic acid and the mixtures thereof. Glycine is the preferred amino acid and can be added to either the directly or indirectly prepared enhanced efficacy aluminum salt with either strontium or calcium, or directly to the zirconium hydroxychloride solution.

As disclosed in U.S. Pat. No. 6,042,816 the presence of an amino or hydroxy acid and a soluble calcium salt is needed in order to stabilize HPLC Band III. Surprisingly, it has been discovered in accordance with the present invention that an aluminum antiperspirant salt with high Band III is obtained through treatment with insoluble calcium oxide alone and the enhanced efficacy aluminum salt solution formed this way provides superior solution viscosity stability. Although the presence of the amino acid facilitates the formation of an initially higher amount of Band III aluminum species, it tends to diminish solution viscosity stability resulting in an undesirable gelling of the solution. Gel formation is not observed from the enhanced efficacy aluminum salt formed through treatment with insoluble, strongly alkaline calcium oxide in the absence of amino acid.

The enhanced efficacy antiperspirant salt of the present invention can be made by either a direct or indirect process.

In the direct process an aqueous aluminum halide or nitrate solution or the corresponding acid solution is heated with an insoluble, strongly alkaline salt of strontium such as strontium hydroxide or strontium oxide or an insoluble, strongly alkaline salt of calcium such as calcium oxide or calcium hydroxide, at temperatures from about 50° C. to about reflux. Aluminum powder is then added to the mixture until the solution with the desired aluminum to anion ratio is obtained. An amino acid such as glycine can be added to the mixture during or at the end of the reaction. In the indirect process, on the other hand, a basic aluminum halohydrate (or nitrate) is heated with an insoluble, strongly alkaline strontium or calcium salts for a suitable period of time. An amino acid such as glycine is not required but may be added, if desired. Thus, in either the direct or indirect process, an amino acid is not required.

Preferred basic aluminum halohydrates (or nitrates) have the formula of $$Al_2(OH)_{6-a}X_a$$

wherein X is Cl, Br, I or $NO_3$, a is from about 1.1 to about 6 at a concentration of about 20% to about 40% by weight of anhydrous solid. It is preferably to have a basic aluminum chlorohydrate solution with aluminum to chloride ratio of about 1.0 to about 1.8, and most preferably from about 1.2 to about 1.6.

A zirconium compound with or without an amino acid can be added to the above enhanced efficacy aluminum antiperspirant solution made with an insoluble, strongly alkaline strontium or calcium salts, at temperatures that may vary from about room temperature (RT) to about reflux, to form an aluminum-zirconium antiperspirant solution with Al:Zr ratio of about 2:1 to about 10:1. The preferred zirconium salt is zirconium hydroxychloride with a chloride to zirconium ratio from about 1.0 to about 2.

The zirconium compounds useful in the present invention are those having the formula $$ZrO(OH)_bX_{2-b}$$

wherein b is a number from 0 to 1.2, X is Cl, Br, I or $NO_3$, with chloride is the most preferred. The zirconium hydroxychloride solution can be prepared by reacting basic zirconium carbonate with hydrochloric acid or zirconyl chloride at an elevated temperature for a certain period of time.

The desired enhanced efficacy aluminum and aluminum-zirconium solutions made according to the invention utilizing an insoluble, strongly alkaline strontium or calcium salts can be dried to a powder by any appropriate means, such as by spray drying, freeze-drying, vacuum drying, and the like, with spray drying being the preferred method.

The resulting compositions of aluminum or aluminum-zirconium salts of enhanced efficacy, made with an insoluble, strongly alkaline strontium or calcium salts have HPLC Band III to Band II area ratios of at least 0.5, preferably of at least 0.7. Optimally, an HPLC Band III to Band II area ratio of at least 0.9 is most preferably attainable. Such compositions also have higher pH values of at least 3.5 when dissolved as 15% by weight aqueous solutions, especially at lower metals to chloride ratio of about 0.9 to about 1.2.

The preferred antiperspirant salts can be suspended in an anhydrous organic base at a concentration of about 10% to about 22% anhydrous solid active. Such solid stick compositions show reduced or no skin irritation, have no acidic smell and are harder in texture compared to those made from low metals to chloride ratio aluminum-zirconium antiperspirant actives, especially compared to those sticks made of antiperspirant compositions that contain calcium chloride.

The degree of the polymerization of aluminum complexes is determined by the size exclusion column that is operated by the High Performance Liquid Chromatography (HPLC). The highest molecular weight Al species are eluted first, designated as Band I or otherwise called peak 1 & 2. Bands II and Bands III or peaks 3 and peak 4 designate intermediate molecular weight Al complexes. Band IV or peak 5 designates the lowest molecular weight Al complexes, including monomers and dimmers. The relative area of one or more peaks is determined in order to characterize the distribution of polymeric species in aluminum complexes formed. The aluminum or aluminum-zirconium antiperspirant salts of the present invention have HPLC Band III to Band II area ratio of at least 0.5, preferably at least 0.7, and most preferably at least 0.9. Preferred compositions also have HPLC Band IV area of at least 15%.

A Phenominex column and a Waters column connected in series are used to obtain a HPLC Chromatograph. Each sample is dissolved in deionized water to form a 2% by weight Al solution. Each sample is filtered through a 0.45 µ filter and chromatographed within 15 minutes using a 0.01N nitric acid solution as the mobile phase.

$^{27}$Al Nuclear Magnetic Resonance (NMR) is selected to identify the structures of different aluminum species in the aluminum or aluminum-zirconium strontium or calcium antiperspirant salts of enhanced efficacy. The antiperspirant salt in solution form is measured as is and the powder is dissolved in deuterated water to form a 10% by weight solution just before the measurement. Data was collected using a Varian Inova 400 instrument at 104.2 MHz.

Generally a sharp peak at chemical shift of about 0 ppm by $^{27}$Al NMR indicates the presence of octahedral coordinated aluminum (Al) monomers and a sharp peak at about 63 ppm indicates the presence of a single tetrahedral coordinated Al in an $Al_{13}$ species. A broad chemical shift at about 72 ppm is an indication of the presence of $Al_{41}$ species. Larger aluminum species usually show chemical shifts that are too broad to be detected. The aluminum-zirconium antiperspirant salts of enhanced efficacy that are formed by treatment with insoluble, strongly alkaline strontium or calcium salts do not show sharp peaks at about 63 ppm indicating the absence of $Al_{13}$ species. Since the presence of $Al_{13}$ species does not indicate enhanced efficacy, it is desirable that they not be present. Preferred aluminum-zirconium strontium or calcium salts of the present invention contain less than 5% $Al_{13}$ species and most preferably contain no $Al_{13}$ species along with about 5% to about 20% aluminum monomers, preferably about 6% to about 15% aluminum monomers.

Direct Preparation Of Basic Aluminum Halohydrate In The Presence Of Alkaline Calcium Salts According to U.S. Pat. No. 5,908,616 basic aluminum halohydrate salts of enhanced efficacy are prepared having Al to anion mole ratio of about 1.2 to about 1.8, preferably from about 1.6 to about 1.7, and a solution concentration of about 30% to about 40% by weight of anhydrous solid with low HPLC Band III to Band II ratio. Higher HPLC Band III to Band II ratio basic aluminum chlorohydrate solutions with Al to chloride ratio of typically 1.9 to 2.1 are formed in the presence of both calcium and glycine as indicated in U.S. Pat. No. 6,042,816. As illustrated in Example 6, an aluminum chlorohydrate solution with HPLC Band III to Band II area ratio of less than 0.2 was formed in the absence of glycine by the direct reaction of aluminum powder with hydrochloric acid aqueous solution in the presence of calcium chloride.

In accordance with the present invention, it has been discovered that in the presence of an insoluble, strongly alkaline calcium salt, basic aluminum halohydrate solutions with Band III to Band II area ratios of at least 0.5, preferably at least of 0.7 are formed by both direct and indirect processes in the absence of amino acid at Al to chloride ratio of about 1.0 to about 1.8. The solutions are stable with respect to both HPLC Band III to Band II area ratio and viscosity of the solution. Preferably the basic aluminum halohydrate (or nitrate) solution has an Al to anion ratio of about 1.0 to about 1.8 and most preferably from about 1.2 to about 1.6. Preferably a greater than 20% by weight of anhydrous solid solutions are made by the direct reaction of aluminum metal with aluminum halide or nitrate or HX, wherein X is Cl, Br, I, and $NO_3$ aqueous solution at elevated temperature for the desired period of time. Preferred insoluble, strongly alkaline calcium salts are calcium oxide, calcium hydroxide and the mixtures thereof. The amount of calcium salt used should be sufficient to provide the Band III to Band II ratio of at least 0.5. Preferably the basic aluminum halohydrate (or nitrate) solution has about 0.1% to about 2% by weight of calcium and most preferably about 0.3% to about 1% by weight of calcium depending on the ratio of aluminum to anion. Generally, less calcium is needed at higher aluminum to anion ratios and the opposite is true at lower ratios. The basic aluminum halohydrate (or nitrate) solutions of enhanced efficacy can be dried to powders, preferably by spray drying.

The invention will be further illustrated by the following Examples. In the Examples, percent anhydrous solid (A.S.) is given as % A.S.

EXAMPLE 1

A Basic Aluminum Chlorohydrate (BAC) solution was prepared by first mixing 563 grams of $32°Be$ aluminum chloride solution (approximately 28% by weight) with 1295 gram of water and 17 grams of calcium oxide at about 80° C. to about 85° C. for about 30 minutes. 125 grams of aluminum powder (99% minimum purity, particle size 75% through 325 mesh) was slowly added to the above solution at 80° C. to 95° C. After about 3 hours the reaction was complete. The reaction mixture was filtered to give a clear colorless solution. The results of the analysis are set forth in Table I below:

TABLE I

| | |
|---|---|
| % Al | 7.77 |
| % Cl | 6.44 |
| pH (15% w/w) | 4.45 |
| Al/Cl ratio | 1.6 |
| % Ca | 0.62 |
| Band III/II ratio | 0.9 |

EXAMPLE 2

In this example, four BAC solutions with different Al to Cl ratio at various calcium contents were prepared in accordance with the method of the present invention and their HPLC patterns were evaluated. The Al to Cl ratio and HPLC Band III to II of each sample are set forth in Table II:

TABLE II

| Al/Cl | % Ca | % A.S. | pH (15% w/w) | Band III/II |
|---|---|---|---|---|
| 0.97* | 1.14 | 35.94 | 3.85 | 0.74 |
| 1.38 | 1.3 | 26.50 | 4.44 | 0.67 |
| 1.57 | 1.01 | 28.12 | 4.40 | 1.06 |
| 1.88 | 0.48 | 27.97 | 4.41 | 1.13 |

*The solution was aged for 1 year at RT.

The BAC solutions reacted with insoluble, strongly alkaline calcium salts are very stable at appropriate Al to Cl ratios and calcium content. However, at higher Al to Cl ratio, i.e., at a ratio of about 1.88, a white precipitate formed within three days at RT. At higher calcium content, such as at about 2.5% by weight of Ca, the BAC solutions gelled up at aluminum to chloride ratios of about 1.4 and 1.6. Not wishing to be bound with any theories, it is believed at higher Al to Cl ratio, or at higher calcium (or strontium) content such as above 2.5, or both, i.e., higher Al to Cl ratio and higher calcium (or strontium) content, the pH of the BAC solutions have been increased so much that the aluminum species become too polymerized to be stable in the solutions.

Preparation Of Basic Aluminum Chlorohydrate In The Presence Of Calcium Oxide Or Strontium Hydroxide And Glycine In accordance with the present invention, it was discovered that the basic aluminum chlorohydrate solutions in the presence of both calcium oxide/glycine and strontium hydroxide/glycine become unstable at Al to Cl ratio of about 1 to about 1.8. The solutions have higher Band III to II ratios than the corresponding BAC solutions without glycine, however, the solutions gelled quickly at RT, usually within one month at RT.

EXAMPLE 3

The BAC solutions are made by mixing varying amounts of calcium oxide with aluminum chloride aqueous solution first, then reacting the solutions with aluminum powder, followed by the addition of glycine. The reactions were carried out at a temperature of about 80° C. to 95° C. for a suitable period of time. The solutions can also be made by indirect process, i.e., heating BAC with calcium oxide and glycine for a certain period of time, preferably reflux the mixture for two hours. The five BAC solutions listed below have about 25% by weight of anhydrous solid and about 5% by weight of glycine. The results are shown below in Table III:

TABLE III

| | Process | Al/Cl | % Ca | Band III/II | Stability |
|---|---|---|---|---|---|
| A | direct | 0.95 | 1.28 | 1.04 | gel/3 wks/RT |
| B | indirect | 1.0 | 0.89 | 1.0 | gel/1 mo/RT |
| C | direct | 1.15 | 1.27 | 2.6 | gel/2 wks/RT |
| D | indirect | 1.36 | 0.91 | 1.84 | gel/1 mo/RT |
| E | direct | 1.55 | 0.62 | 1.74 | grl/1 wk/RT |

The stability results of BAC solutions in the presence of calcium oxide and glycine are different from what had been observed by U.S. Pat. No. 6,042,816, in which it claimed that an aqueous solution of an enhanced efficacy antiperspirant salt can be stabilized by the inclusion of a soluble calcium salt such as calcium chloride and an amino acid. By "stabilized" is meant that the peak 4 (or Band III) to peak 3 (or Band II) ratio (HPLC area) will remain 0.5 or higher for at least one month at room temperature as demonstrated by Example 2 where 25% by weight of anhydrous solid of ACH' solutions are stable in the presence of calcium chloride dihydrate and glycine.

The observed differing stability results obtained by the process of the present invention compared to those described in the disclosure of U.S. Pat. No. 6,042,816, indicate that different antiperspirant salt solutions are formed in the presence of different calcium species, i.e., those formed from soluble, neutral salts vs. insoluble, strongly alkaline salts, and at different Al to Cl ratios, i.e., about 1.9 to about 2.1 vs. about 1.0 to about 1.6. Not wishing to be bound with any theories, it is thought that the addition of calcium oxide and glycine to the BAC solutions changes the structures of the aluminum species, which alters the kinetics of the BAC solutions.

EXAMPLE 4

In this example, four BAC solutions with different Al to Cl ratios at various strontium contents were prepared by direct process similar to that of Example 3. The insoluble, strongly alkaline strontium salt used in the example is strontium hydroxide. The BAC-Sr-Glycine solutions shown below contain about 25% by weight of anhydrous solid and about 5% by weight of glycine. The results are set forth below in Table IV:

TABLE IV

|   | Al/Cl | % Sr | Band III/II | Stability |
|---|---|---|---|---|
| F | 1.0 | 2.0 | 0.57 | gel/3 wks/RT |
| G | 1.25 | 1.26 | 0.78 | gel/10 days/RT |
| H | 1.36 | 1.06 | 0.82 | gel/3 wks/RT |
| I | 1.6 | 1.24 | 0.97 | gel/3 wks/RT |

Preparation Of High pH Aluminum-Zirconium-Glycine Salt Solutions Of Enhanced Efficacy In The Presence Of Calcium Oxide Or Strontium Hydroxide It has been discovered in accordance with the present invention that the aluminum-zirconium-glycine solutions in the presence of calcium oxide or strontium hydroxide have higher pH values and are stable with respect to both HPLC Band III to Band II area ratio and viscosity of the solutions. The above solutions were prepared with BAC having Al to chloride ratio of about 1 to about 1.6. $^{27}$Al NMR of the solutions show no sharp peak at about 63 ppm which indicates the absence of $Al_{13}$ species that are believed to detract from the enhanced efficacy.

The aluminum-zirconium antiperspirant can be prepared by three methods. The first method involves reacting a basic aluminum halohydrate (or nitrate) with calcium oxide in the presence of glycine or with strontium hydroxide in the presence of glycine with a zirconium complex. The second method includes reacting a basic aluminum halohydrate (or nitrate) solution with calcium oxide or strontium hydroxide followed by addition of zirconium hydroxychloride glycinate solution at elevated temperature such as about reflux. The third method includes reacting a zirconium compound such as zirconyl chloride with calcium oxide or strontium hydroxide in aqueous solution at about RT to about reflux, adding a polyhydric alcohol to the solution and mixing with a BAC solution at elevated temperature for certain period of time until the enhanced efficacy salt forms. The basic aluminum chlorohydrate solution has an Al to Cl ratio of about 1 to about 1.8, preferably from about 1 to about 1.6. The zirconium complex usually has a chloride to zirconium ratio of about 0.8 to about 2.0, preferably from about 1 to about 2.0. The aluminum-zirconium antiperspirant of enhanced efficacy has Al to Zr ratio of about 2 to about 10.

EXAMPLE 5

525 grams of zirconyl hydroxychloride solution and 4 grams of water were treated with 2041 grams basic aluminum chlorohydrate-glycine calcium reaction product (Al/Cl ratio of 0.95) prepared in Example 3 and mixed at RT for 1 hour. Part of the solution was spray dried and micronized. The results are set forth in Table V.

TABLE V

|   | Solution | Powder |
|---|---|---|
| Al/Zr ratio | 4.7 | 4.8 |
| M/Cl ratio | 0.95 | 0.99 |
| % A.S. | 31.24 | 72.36 |
| % Ca | 1.02 | 2.32 |
| pH (15% w/w) | 3.87 | 3.64 |
| particle size (% < 10 micron) | — | 98.4 |
| Band III/II area ratio (fresh) | 1.23 | 1.29 |
| Band III/II area ratio (1 MO) | 1.49 | — |

Figure 1:
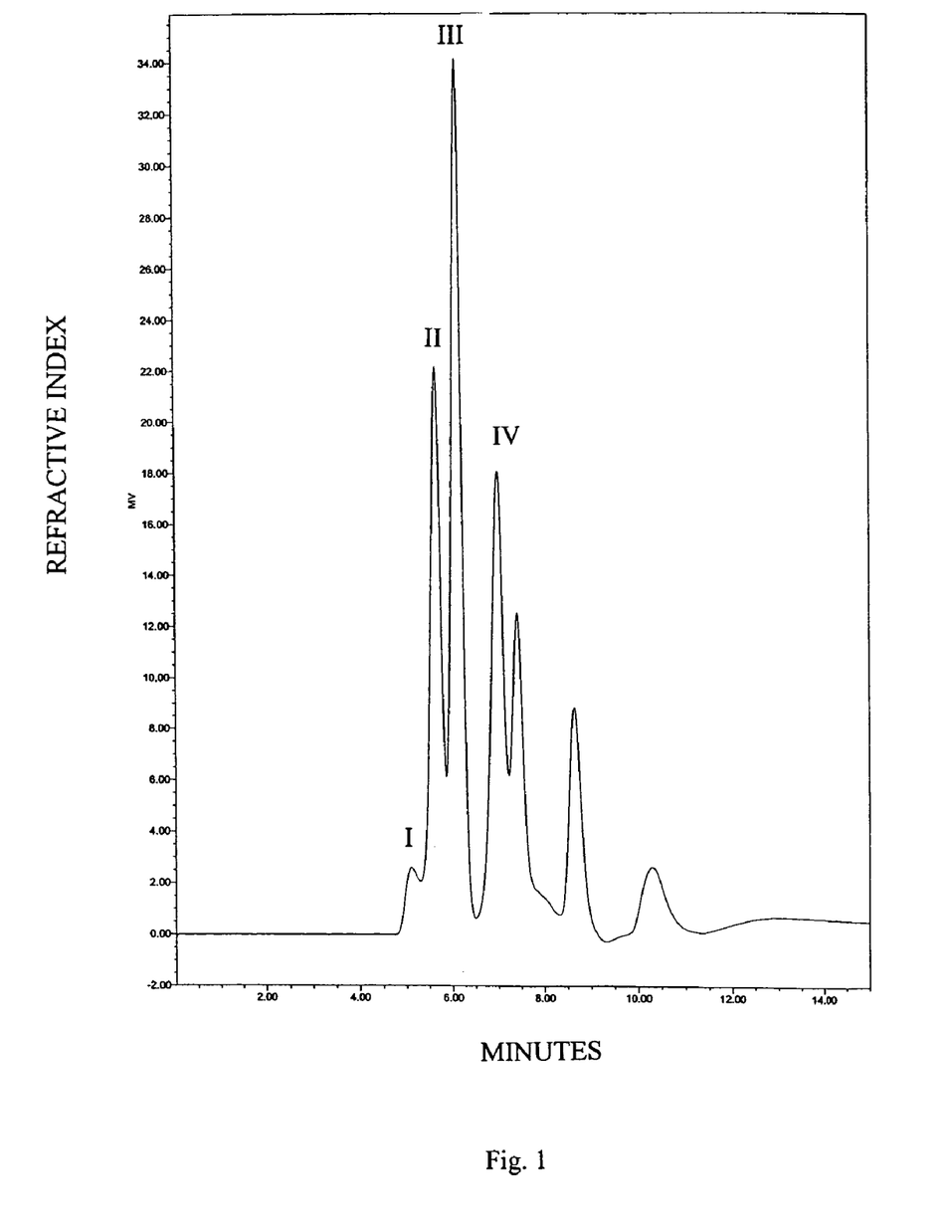
FIG. 1 is a HPLC chromatogram of the Al—Zr-Glycine solution prepared in the presence of calcium oxide according to Example 5.
Figure 2:
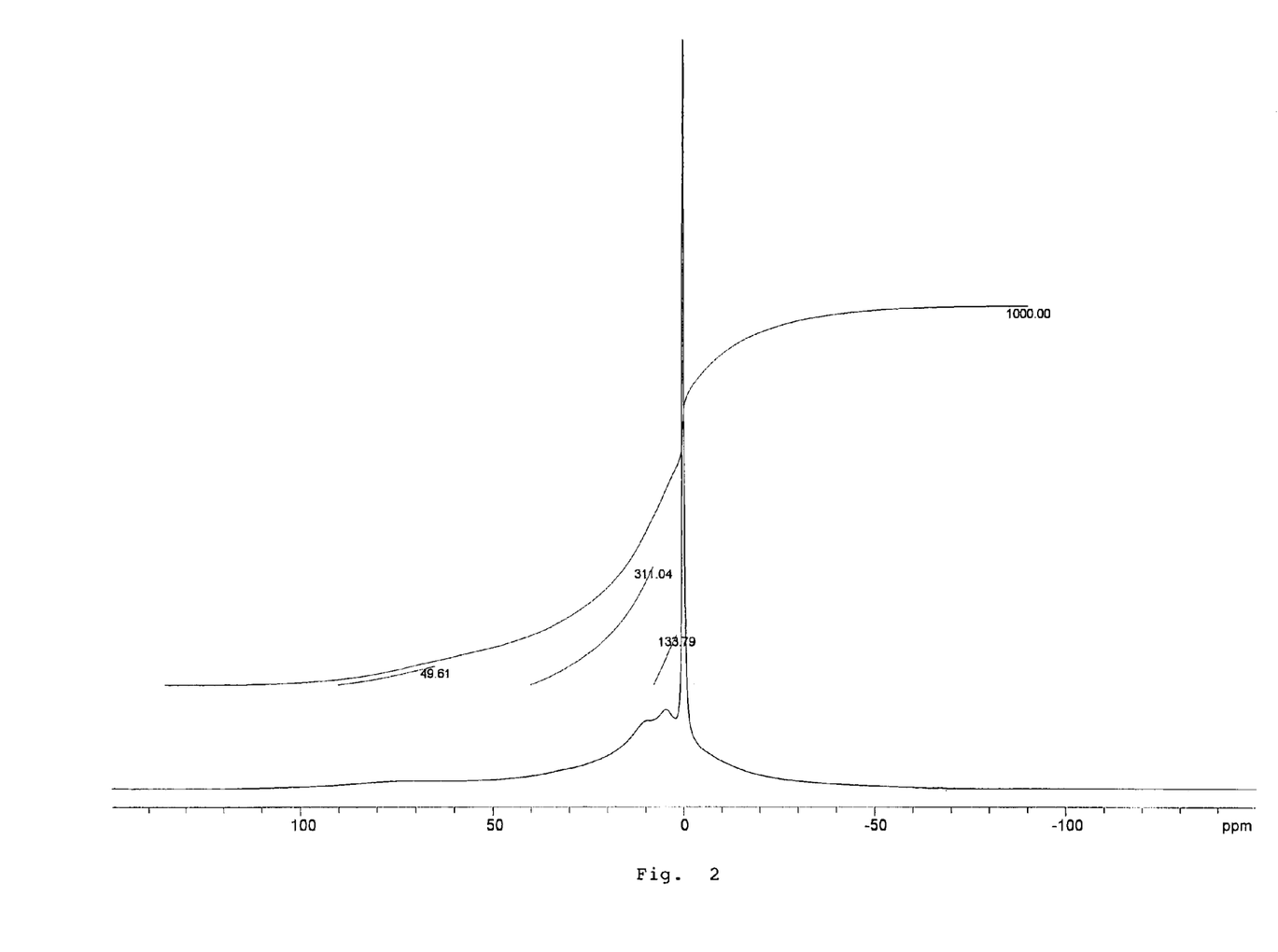
FIG. 2 is the $^{27}$Al NMR chromatogram of the same solution demonstrated in FIG. 1.
Figure 3:
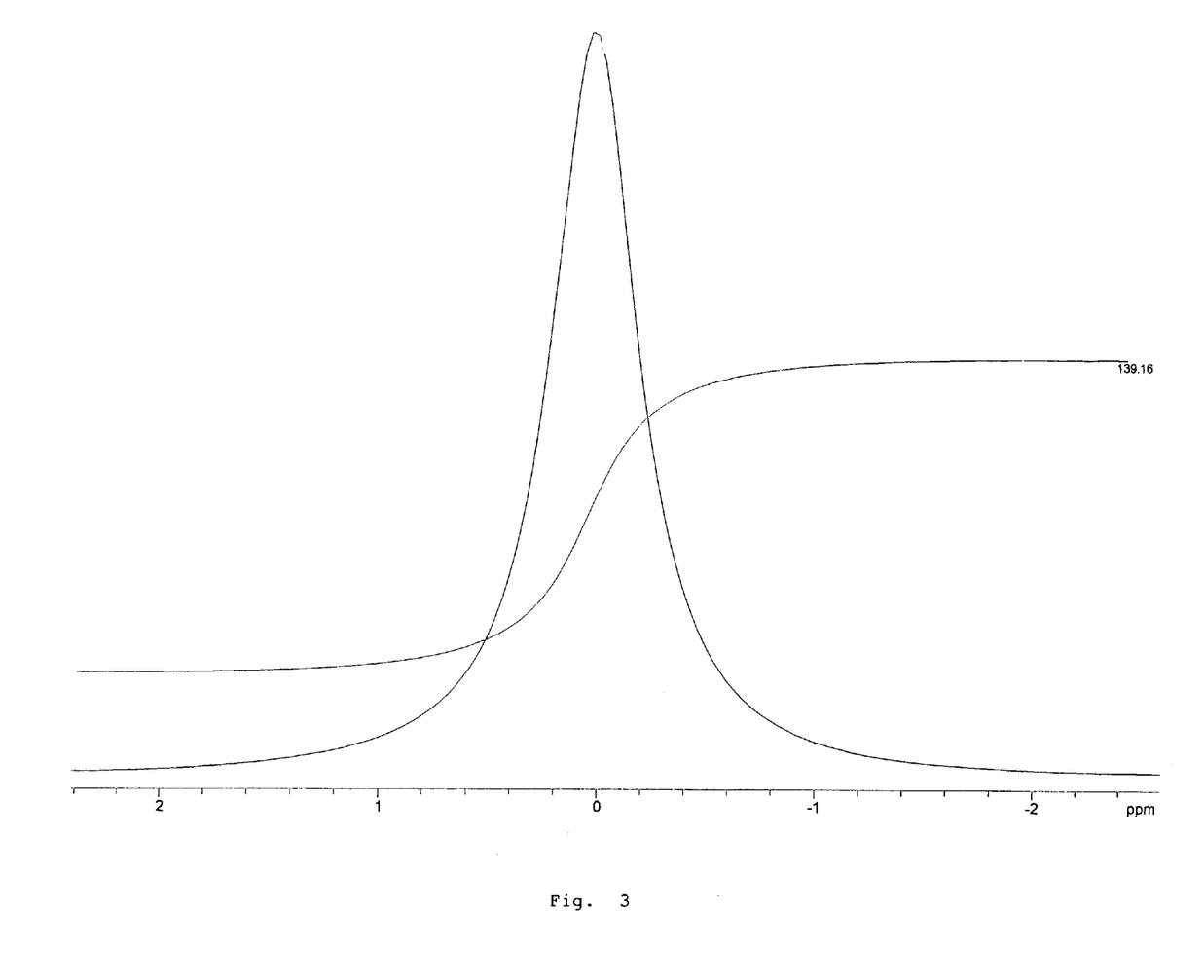
FIG. 3 is the $^{27}$Al NMR chromatogram of FIG. 2 for the region from −2.5 to +2.5 ppm.

The HPLC chromatograph is shown in FIG. 1 and the $^{27}$Al NMR of the solution are shown in FIG. 2 and FIG. 3. The $^{27}$Al NMR of the Al—Zr-glycine calcium solution shows the absence of $Al_{13}$ species that are believed to detract from the enhanced efficacy.

EXAMPLE 6

In this example, four Al—Zr-glycine calcium products were prepared in accordance with the method of the present invention. The method of the preparation of the solution is similar to what is described in Example 5. The basic aluminum chlorohydrate-glycine calcium products are prepared by both direct and indirect reactions, in which the BAC solutions have Al to Cl ratios of about 1 to about 1.6. The results are set forth in Table VI:

TABLE VI

|   |   |   |   |   |   | Band III/II | |
|---|---|---|---|---|---|---|---|
|   | Al/Zr | M/Cl | % A.S. | % Ca | pH (15% w/w) | (fresh) | (~1 MO) |
| J | 4.7 | 0.95 | 31.10 | 1.02 | 3.90 | 1.10 | 1.61 |
| K | 4.7 | 1.15 | 30.18 | 0.81 | 4.00 | 1.69 | 2.17 |
| L | 5.1 | 1.27 | 30.77 | 0.74 | 4.10 | 1.54 | 1.56 |
| M | 4.7 | 1.38 | 29.04 | 0.48 | 4.14 | 1.76 | 1.12 |

EXAMPLE 7

Two Al—Zr—Sr-Glycine products were prepared by direct process. Insoluble strontium hydroxide was used. As demonstrated in Table VII more strontium hydroxide was consumed in order to increase the solution pH values when compared to those solutions adjusted with calcium oxide.

TABLE VII

|   |   |   |   |   |   | Band III/II | |
|---|---|---|---|---|---|---|---|
|   | Al/Zr | M/Cl | % A.S. | % Sr | pH (15% w/w) | (fresh) | (1 MO) |
| N | 4.7 | 1.40 | 28.45 | 0.97 | 4.16 | 0.91 | 0.71 |
| O | 8.0 | 1.45 | 27.45 | 1.06 | 4.29 | 0.97 | 0.85 |

Comparison Of Al—Zr-Glycine Salts In The Presence Of Calcium Oxide vs. Calcium Chloride And In The Absence Of Calcium Salts

EXAMPLE 8

Two Al—Zr-Glycine salts that contain calcium were made according to present invention. The Al—Zr-Glycine salts were made with either calcium oxide or calcium chloride and prepared under the same conditions as in Example 5. The Al—Zr-glycine salt was made by the conventional method, i.e., diluting and refluxing a BAC solution with Al to Cl ratio of 1.39 and cooling the solution to RT, mixing the solution with zirconium hydroxychloride glycinate solution and spray drying the solution. The results are set forth below in Table VIII.

TABLE VIII

|  | P | Q | R |
|---|---|---|---|
| % Ca | — | 1.75 | 2.04 |
| $CaCl_2$ | — | yes | — |
| CaO | — | — | yes |
| Glycine/Zr | 1.14 | 1.10 | 1.17 |
| Al/Zr | 4.9 | 5.0 | 4.8 |
| M/Cl | 1.23 | 1.18* | 1.16 |
| % A.S. | 75.0 | 70.0 | 74.2 |
| pH (15% w/w) | 3.44 | 3.35 | 3.76 |
| Band III/II | 0.5 | 2.4 | 1.6 |

*Cl from $CaCl_2$ is excluded.

EXAMPLE 9

The above three powders were formulated into solid sticks in order to compare the hardness of the sticks. Each of the compositions is prepared by heating the gelling agents, mixing with the cyclomethicone and other ingredients and cooling the mixture to form a solid stick. The hardness of the sticks is measured on Chatillon TCD 200 Texture Analyzer. As shown in Table IX, the hardness of the stick is increased substantially by the use of the insoluble calcium oxide in the preparation of the active.

TABLE IX

|  | Weight Percent | | |
|---|---|---|---|
|  | S | T[a] | U[b] |
| Active | 20.00 | 20.00 | 20.00 |
| Cyclomethicone (DC 245) | 36.00 | 36.00 | 36.00 |
| Stearyl Alcohol | 20.00 | 20.00 | 20.00 |
| Hydrogenated Castor Oil | 5.00 | 5.00 | 5.00 |
| $C_{12-15}$ Allyl Benzoate | 17.50 | 17.50 | 17.50 |
| PEG-8 Distearate | 1.50 | 1.50 | 1.50 |
| Stick Hardness (grams) | 3138 | 2928 | 3683 |

[a]$CaCl_2$
[b]CaO

Although the invention has been described in terms of particular embodiments, blends of one or more of the various reactants and additives described herein can be used, and substitutes therefor, as will be known to those skilled in the art. Thus, the invention is not meant to be limited to the details described herein, but only by the scope of the appended claims.

What is claimed:

1. A method of making an antiperspirant liquid composition having improved efficacy and a pH value of at least 3.5 when dissolved as 15% by weight aqueous solution and wherein the composition comprises an antiperspirant active selected from
   (i) basic aluminum salts having the formula $Al_2(OH)_{6-a}X_a$ wherein X is Cl, Br, I or $NO_3$, a is from about 1.1 to about 6, at a concentration of about 20% to about 40% by weight of anhydrous solid and having an aluminum to anion mole ratio of about 1.0 to about 1.8 and
   (ii) aluminum-zirconium salts having an Al:Zr ratio of from about 2:1 to about 10:1 that are obtained by adding to the salts of formula (i) a zirconium compound selected from those having the formula $ZrO(OH)_bX_{2-b}$ wherein b is a number from 0 to 1.2, and X is Cl, Br, I or $NO_3$,
the steps comprising:
   (1) treating the aqueous reaction mixture of said antiperspirant active with from about 0.1% to about 2% by weight of an additive selected from the group consisting of strongly alkaline water insoluble calcium and strontium compounds and mixtures thereof, and
   (2) mixing and reacting said mixture, wherein said additive is activated by contact with said antiperspirant active, until a stable solution with respect to HPLC Band III and Band II area ratio of at least 0.5 is obtained.

2. The method of claim 1 wherein the reacting step (2) is maintained until an HPLC Band III and Band II area ratio of at least 0.7 is obtained.

3. The method of claim 1 wherein the antiperspirant comprises the basic aluminum salts of formula (i).

4. The method of claim 1 wherein the antiperspirant composition comprises the aluminum-zirconium salts of formula (ii).

5. The method of claim 4 wherein the reaction of step (2) is maintained until an HPLC Band III and Band II area ration of at least 0.9 is obtained.

6. The method of claim 3 wherein the reacted liquid composition contains from about 25% to about 35% by weight of the salt.

7. The method of claim 3 wherein the reacted liquid composition contains from about 25% to about 35% by weight salt and up to about 8% by weight of an amino acid.

8. The method of claim 4 wherein the reacted liquid composition contains from about 25% to about 35% by weight salt and up to about 8% by weight of an amino acid.

9. The method of claim 4 wherein the reacted liquid composition contains from about 25% to about 35% by weight salt and from about 3% to about 6% by weight of an amino acid.

10. The method of claim 1 wherein the insoluble, strongly alkaline compound is selected from strontium hydroxide, strontium oxide, calcium oxide, calcium hydroxide and mixtures thereof.

11. The method of claim 7 wherein the amino acid is glycine.

12. The method of claim 8 wherein the amino acid is glycine.

13. The method of claim 4 wherein a basic aluminum halohydrate (or nitrate) is reacted with calcium oxide and a zirconium compound in the presence of glycine.

14. The method of claim 4 including reacting a basic aluminum halohydrate (or nitrate) solution with calcium oxide and a zirconium hydroxyhalohydrate (or nitrate) glycinate solution at a temperature of from about room temperature to about reflux temperature.

15. The method of claim 4 wherein the zirconium compound (ii) is reacted with calcium oxide at a temperature of from about room temperature to about reflux temperature, adding a polyhydric alcohol to the solution and mixing the solution with basic aluminum halohydrate (or nitrate) for a period of time sufficient to provide the enhanced efficacy salt.

16. The method of claim 1 wherein the resultant stable solution from step (2) is dried to a powder form.

17. The method of claim 3 wherein the resultant stable solution form step (2) is spray dried.

18. The method of claim 4 wherein the resultant stable solution from step (2) is spray dried.

19. The method of claim 17 wherein from about 5% to about 25% of the spray dried product is admixed with a silicone oil and an aliphatic alcohol; heated until a homogenous blend is obtained, poured into a stick-antiperspirant mold form and solidified.

20. The method of claim 18 wherein from about 5% to about 25% of the spray dried product is admixed with a silicone oil and an aliphatic alcohol; heated until a homogenous blend is obtained, poured into a stick-antiperspirant mold form and solidified.

21. A product obtained by the method of claim 1.
22. A product obtained by the method of claim 3.
23. A product obtained by the method of claim 4.
24. A product obtained by the method of claim 6.
25. A product obtained by the method of claim 7.
26. A product obtained by the method of claim 8.
27. A product obtained by the method of claim 9.
28. A product obtained by the method of claim 10.
29. A product obtained by the method of claim 11.
30. A product obtained by the method of claim 12.
31. A product obtained by the method of claim 13.

32. An aluminum-zirconium antiperspirant composition prepared with calcium oxide according to claim 4 wherein the reaction of step (2) is maintained until a product having a metal to chloride ratio of from about 1.0 to about 1.2 and a pH of at least 3.5 is obtained.

* * * * *